US005933819A

United States Patent [19]
Skolnick et al.

[11] Patent Number: 5,933,819
[45] Date of Patent: Aug. 3, 1999

[54] PREDICTION OF RELATIVE BINDING MOTIFS OF BIOLOGICALLY ACTIVE PEPTIDES AND PEPTIDE MIMETICS

[75] Inventors: Jeffrey Skolnick; Mariusz Milik, both of San Diego, Calif.; Andrezej Kolinski, Warsaw, Poland

[73] Assignee: The Scripps Research Institute, La Jolla, Calif.

[21] Appl. No.: 08/862,192

[22] Filed: May 23, 1997

[51] Int. Cl.$^6$ ..................................................... G06F 15/18
[52] U.S. Cl. ................................................. 706/21; 706/31
[58] Field of Search ................................ 706/16, 21, 20, 706/31

[56] References Cited

U.S. PATENT DOCUMENTS 5,862,304   1/1999   Ravdin et al. ............................. 706/20

OTHER PUBLICATIONS

T–Masters, "Practical Neural Network Recipes in Ctt", Acad. Press Inc., Boston 1993.

Metfessel etal, "Pattern Recognition in the predicition of protein structure class," IEEE Proceedings of the 26th Hawaii International Conference on system sciences, Jan. 1993.

Søren Kamaric Riis, "Combining Neural Networks for protein secondary structure prediction," IEEE ICNN, Nov.–Dec. 1995

Ruggerio etal, "Peptides secondary structure prediction with Neural Network: A criterion for Building Appropriate Learning Sets,", IEEE Transactions on Biomedical Engineering, vol. 40, No. 11, Nov. 1993.

Willcox et al, "Generalization of protein structure from Sequence Using a Large Scale Backpropagation Network,", IEEE IJCNN, Jun. 1989.

Kneller, "Improvements in Protein Secondary Structure Prediction by an Enhanced Neural Network," J. Mol. Biol., vol. 214, 1990.

Holley et al, "Neural Networks for protein structure prediction," Methods in Enzymology, vol. 202, 1991.

Holley et al., "Protein Secondary Structure Prediction with Neural Network, " Proc. Natl. Acad. Sci., vol. 86, Jan. 1989.

Qian et al, "Predicting the secondary structure of Globular protein Using Neural Network Models," J. Mol. Biol., vol. 202, 1988.

Taylor, W.R., "The Classification of Amino Acid Conservation", J. Theor. Biol., vol. 119, No. 1, pp. 205–218, Mar. 7,. 1986.

Hush, D.R., et al., "Progress in Supervise Neural Networks: What's New Since Lippman?", IEEE Signal Processing, pp. 8–36, Jan. 1993.

J. Skolnick, et al., "A Method for Prediction of Protein Structure from Sequence," Current Biology, vol. 3, pp. 414–423, Jul. 1, 1993.

Ruppert, J., et al., "Prominent Role of Secondary anchor Residues in Peptide Binding to HLA–A2.1 Molecules", Cell, vol. 74, No. 5, pp. 929–937, Sep. 10, 1993.

Lohmann, R., et al., "Neural network model for the prediction of membrane–spanning amino acid sequences", Protein Science, vol. 3, No. 9, pp. 1597–1601, Sep. 1994.

(List continued on next page.)

Primary Examiner—Robert W. Downs
Attorney, Agent, or Firm—Fish & Richardson P.C.

[57] ABSTRACT

A general neural network based method and system for identifying peptide binding motifs from limited experimental data. In particular, an artificial neural network (ANN) is trained with peptides with known sequence and function (i.e., binding strength) identified from a phage display library. The ANN is then challenged with unknown peptides, and predicts relative binding motifs. Analysis of the unknown peptides validate the predictive capability of the ANN.

21 Claims, 3 Drawing Sheets

OTHER PUBLICATIONS

Milik, M., et al., "An Object–Oriented Environment for Artifical Evolution of Protein Sequences: The Example of Rational Design of Transmembrane Sequences", *Evolutionary Programming IV: Proceedings from the Fourth Annual Conference on Evolutionary Programming,* McDonnell, J.R., et al., eds., pp. 603–613, MIT Press, Cambridge, 1995.

Schneider, G., et al., "Peptide Design in Machina: Development of Artificial Mitochondrial Protein Precursor Cleavage Sites by Stimulated Molecular Evolution", *Biophysical Journal,* vol, 68, pp. 434–447, Feb. 1995.

Tomii, K., et al., "Analysis of amino acid indices and mutation matrices for sequence comparison and structure prediction of proteins", *Protein Engineering,* vol. 9, No. 1, pp. 27–36, Jan. 1996.

Shneider et al, "Prediction of the Secondary Structure of proteins from the Amino Acid Sequence with Artificial Neural Networks," Angew. Chem. Int. Ed. Engl. vol. 32, 1993.

Rost et al, "Improved prediction of protein Secondary structure by use of Sequnce Profiles and Neural Networks," Proc. Natl. Acad. Sci., vol. 90, Aug. 1993.

PREDICTION OF RELATIVE BINDING MOTIFS OF BIOLOGICALLY ACTIVE PEPTIDES AND PEPTIDE MIMETICS

BACKGROUND OF THE INVENTION

1. Field of the Invention

This invention relates to computer-assisted analysis of biological molecules, particularly of biologically active peptides and peptide mimetics.

2. Description of Related Art

With the ever increasing plethora of biological information, the new branch of biological sciences called bioinformatics has become increasingly important. Bioinformatics seeks to translate the mass of protein (polypeptide) sequence information into knowledge of structure and more importantly, function.

One category of peptides where structure and function information would be useful are Class I major histocompatiblity complex (MHC) molecules (in humans, the MHC is called HLA). MHC molecules are cell surface proteins that present bound peptides. These peptides are analyzed by immuno-surveillant cytotoxic T-cells (CTLs) to identify foreign or unhealthy cells for removal. Understanding this process is important, as it constitutes the primary immunological defense against viruses and perhaps tumor causing cells. It is also a major component responsible for transplant rejection. A. Townsend and H. Bodmer, *Annu. Rev. Immunol.* 7, 601 (1989); J. W. Yewdell and J. R. Binnink, *Adv. Immunol.* 52, 1 (1992). Since the affinity of the bound peptides largely determines the stability of the expressed class I molecules and their recognition by CTLs, it is crucial to determine the rules of peptide binding by class I molecules. Analyses of peptides eluted from class I MHC molecules reveal that they are short, usually 8–10 amino acids long, with particular amino acids occurring in specific, anchor positions with a very high frequency. Highly conserved pockets accommodate these anchor amino acids as well as the peptide amino and carboxy termini. The carboxy terminal pocket is considerably less constraining than the amino terminus (M. Matsumura, Y. Saito, M. R. Jackson, E. S. Song and P. A. Peterson, *J. Biol. Chem.* 267(33), 23589 (1992); E. J. Collins, E. N. Garboczi and D. C. Wiley, *Nature* 371, 629 (1994)), suggesting the possibility of using a phage display analysis for peptide screening.

Binding analyses with synthetic peptides have confirmed the importance of the anchor residues but have also revealed amino acid preferences at other positions. These secondary anchor residues can have profound effects on binding affinities, as peptide binding to human class I molecules can vary by over four orders of magnitude. Furthermore, combinations of anchor amino acids are restricted, making the binding rules complex. Hence predictions based solely on anchor amino acids are at best about 20% accurate. J. Ruppert, J. Sidney, E. Celis, R. T. Kubo, H. M. Grey and A. Sette, *Cell* 74, 929 (1993). It would be desirable to have an analysis that tests a large number of peptide sequences and considers the correlated effects of amino acids.

Artificial intelligence and pattern recognition methods may prove to be powerful tools in the bioinformatics field. For example, an artificial neural network (ANN) has been successfully applied to predict mitochondrial precursor cleavage sites (G. Schneider, J. Schuchhardt and P. Wrede, *Biophys. J* 68, 434 (1995)) and membrane-spanning amino acid sequences (R. Lohmann, G. Schanider, D. Behrens and P. Wrede, *Protein Science* 3,1597 (1994); M. Milik and J. Skolnick, in: "*Proceedings of Fourth Annual Conference on Evolutionary Programming*", MIT Press, La Jolla (1995)). However, to date, ANN analysis has not been successfully applied to prediction of binding motifs of biologically active peptides and peptide mimetics. The present invention provides a method and system for accomplishing this goal.

SUMMARY OF THE INVENTION

The invention comprises a general neural network based method and system for identifying relative peptide binding motifs from limited experimental data. In particular, an artificial neural network (ANN) is trained with peptides with known sequence and function (i.e., binding strength) identified from a phage display library. The ANN is then challenged with unknown peptides, and predicts relative binding motifs. Analysis of the unknown peptides validate the predictive capability of the ANN.

In one example, the training peptides bind to mouse MHC class I molecule H2-K$^b$. Blind testing (e.g., on chicken ovalbumin) correctly identified strongly binding peptides, and their relative binding strengths, in 5 of the 7 top scoring predictions from the test procedure. Upon validation analysis, the top scoring peptide was the known immunodominant peptide. Further, the second best binding peptide, since it lacked characteristic anchor residues, would have been missed using standard statistical approaches. The ability to predict antigens that bind MHC represents a significant advance in the development of vaccines and T-cell based therapeutics.

The details of the preferred embodiment of the present invention are set forth in the accompanying drawings and the description below. Once the details of the invention are known, numerous additional innovations and changes will become obvious to one skilled in the art.

BRIEF DESCRIPTION OF THE DRAWINGS

Like reference numbers and designations in the various drawings indicate like elements.

DETAILED DESCRIPTION OF THE INVENTION

Throughout this description, the preferred embodiment and examples shown should be considered as exemplars, rather than as limitations on the present invention.

Introduction

The invention will be described using an example of an artificial neural network (ANN) system used to predict relative binding motifs of peptides that bind to MHC class I molecules. However, the process is general and can be applied to any peptide system. An important aspect of the present invention is the inclusion of both experimental and theoretical aspects of the problem into one, coherent procedure. Preliminary results from the ANN analysis improved the interpretation of results from phage display experiments, and later experimental methods were used in blind tests of the ANN classification scheme.

Artificial Neural Networks

Artificial neural networks can be used to recognize patterns and "signatures" in data streams. An ANN differs from other signal processing algorithms in that it does not assume any underlying model. Rather, an ANN "learns" to detect patterns by generating a model in response to input test data having known patterns, features, or other characteristics of interest in classifying the input data. An ANN can be trained relatively easy and repeatably. Because an ANN learns to detect patterns or correlations, ANNs are very flexible and adaptable to a wide variety of situations and conditions. This flexibility and adaptability gives artificial neural networks a significant advantage over other data classification techniques. For further information on the architecture and training of multi-layer perceptron (MLP) adaptive artificial neural networks, see "Progress in Supervised Neural Networks" by Don Hush and Bill Home, published in *IEEE Signal Processing* (January 1993).

Figure 1:
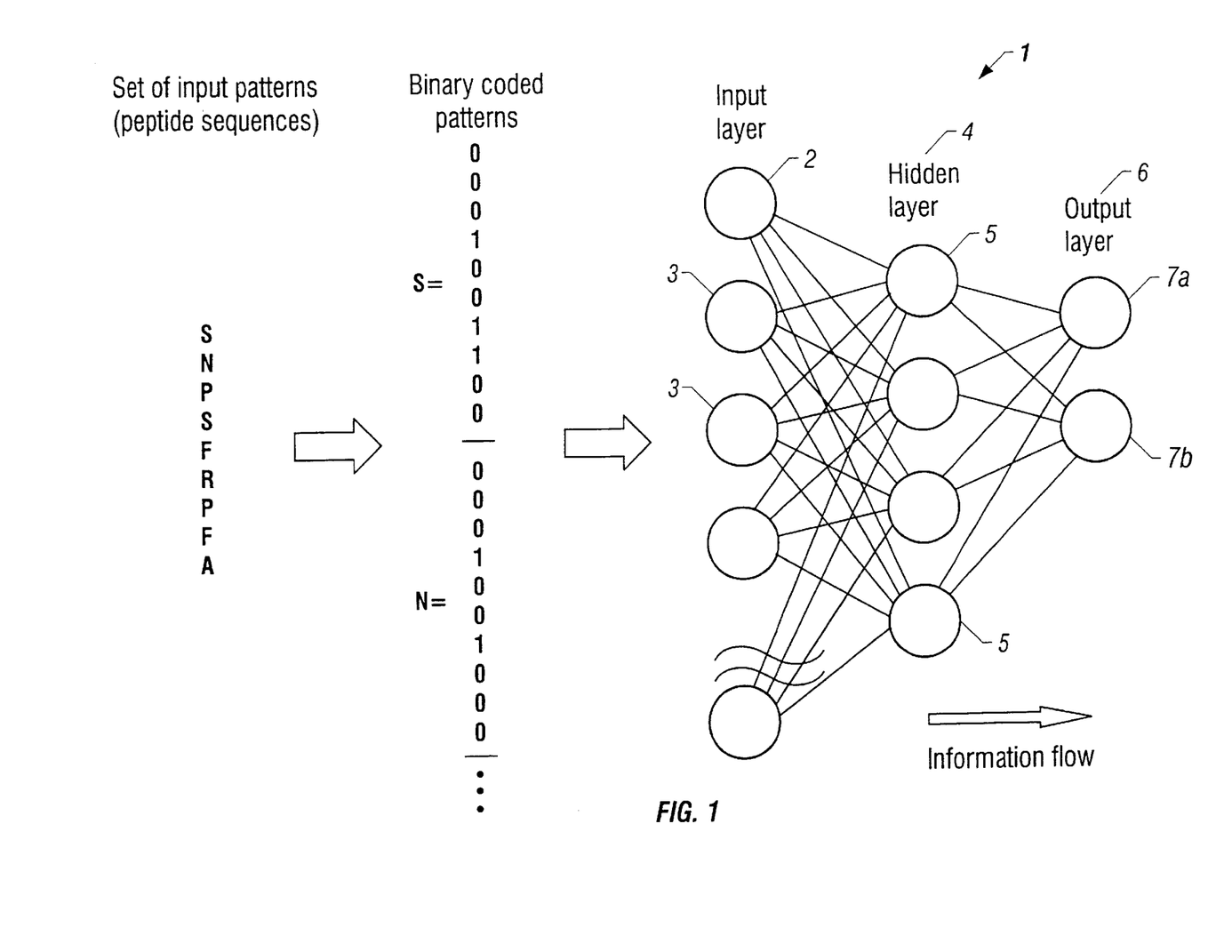
FIG. 1 is a schematic view of the preferred peptide sequence coding scheme and the ANN architecture of the invention.

FIG. 1 is a schematic view of the preferred peptide sequence coding scheme and the ANN architecture of the invention. Shown is a standard multi-layer perceptron ANN 1 trained by back-propagation (BP) of error. D. Rumelhart, J. McClelland and the PDP Research Group, *"Parallel Distributed Processing"*, MIT Press, Cambridge (1986). The ANN 1 includes an input layer 2 comprising a plurality of input units 3, a hidden layer 4 comprising a plurality of hidden units 5, and an output layer 6 comprising a plurality of output units 7. In the preferred embodiment, the number of output units is two, denoted 7a and 7b. Each unit 3, 5, 7 is a processing element or "neuron", coupled by connections having adjustable numeric weights or connection strengths by which earlier layers influence later ones to determine the network output.

Prior to using the ANN 1 to classify actual input data, the parameters of the ANN 1 are adjusted by applying pre-characterized training data to the ANN 1. That is, training data is selected such that particular features are known to present or known to be absent. In the invention, such data comprises an appropriately coded set of input patterns (i.e., known peptide sequences having known binding affinities). See below for a discussion of the preferred coding.

Phage Display

In order to obtain training data for an ANN, a study was initiated with a peptide phage display binding analysis of the mouse MHC class I molecule $K^b$. Soluble $K^b$ was purified from transfected Drosophila cells. Phage display analysis has been used previously to identify MHC class II molecule binding peptides. J. Hammer, B. Takacs and F. Sinigaglia, *J. Exp. Med.* 176, 1007 (1992). Phage display libraries were obtained from Dr. G. P. Smith of the Division of Biological Sciences for the University of Missouri and the analyses were performed essentially as described in the art (S. F. Parmeley, and G. P. Smith, *Gene* 73, 305 (1988); J. K. Scott and G. P. Smith, *Science* 249, 386 (1990); G. P. Smith personal communication). From the phage display, the sequences of 181 $K^b$ binding peptides and their relative binding affinities were obtained along with the sequences of 129 non-binding sequences.

Coding Procedure

The first step in the training of an ANN in accordance with the invention is the translation of peptide sequences into an appropriate representation. The most straightforward approach is to represent every residue by its name. However, this approach has many disadvantages. First, this would result in a large input layer 2, increasing the probability of overfitting with loss of predictive ability by the ANN 1. T. Masters *"Practical Neural Network Recipes in C++"*, Acad. Press Inc. Boston (1993). Second, the similarities of certain amino acids would be lost. For example, the relationship between leucine and either isoleucine or lysine would be treated the same. Encoding such interrelationships (K. Tomii and M, Kanehisa, *Protein Eng.* 9, 27 (1996)) should increase the level of ANN generalization. Thus, a representation was chosen based upon the amino acid features presented in Tables 1A. W. R. Taylor, *J. Theor. Biol.* 119, 205 (1986). Table 1A defines 10 features associated with various amino acids (represented by standard one letter codes). Table 1B then maps each of the 20 natural amino acids as a vector of 10 binary numbers, each numeric position corresponding to the feature mapping in Table 1A. A "1" indicates that the corresponding property is present. A "0" indicates that the corresponding property is absent.

TABLE 1A

Clustering of amino acids according to their physico chemical features

| No. | Feature | amino acid one-letter codes |
| --- | --- | --- |
| 0 | hydrophobic | HWYFMLIVCAGTK |
| 1 | aliphatic | LIV |
| 2 | aromatic | FYWH |
| 3 | polar | TSNDEQURKHWY |
| 4 | charged | DERKH |
| 5 | positive | RKH |
| 6 | small | PVCAGTSND |
| 7 | tiny | AGS |
| 8 | glycine | G |
| 9 | proline | P |

TABLE 1B

Feature based binary coding of amino acids

| amino acid | feature based code 0123456789 |
| --- | --- |
| G | 1000001110 |
| A | 1000001100 |
| V | 1100001000 |
| L | 1100000000 |
| I | 1100000000 |
| S | 0001001100 |
| T | 1001001000 |
| D | 0001101000 |
| N | 0001001000 |
| K | 1001110000 |
| E | 0001100000 |
| Q | 0001000000 |
| R | 0001110000 |
| H | 1011110000 |
| F | 1010000000 |
| C | 1000001000 |
| W | 1011000000 |
| Y | 1011000000 |
| M | 1000000000 |
| P | 0000001001 |

For example, in FIG. 1, a peptide having the amino acid sequence of "SNPSFRPFA" is coded as a binary pattern beginning with the binary pattern for "S", and continuing with the binary pattern for "N", etc. Of course, other mappings are possible, as well as other, fewer, and/or additional features.

ANN Training

As indicated in FIG. 1, the ANN 1 has two output nodes 7a, 7b. The output signal of the ANN 1 was defined as follows:

"00" (both nodes 7a, 7b off) denotes a non-binding sequence

"10" (first node 7a off, second node 7b on) denotes a weakly binding sequence

"11" (both nodes 7a, 7b on) denotes a strongly binding sequence.

The 181 $K^b$ binding peptides were divided into strong and weak binding classes, according to their respective experimentally measured binding constants. Additionally, the 129 peptides having no detectable affinity for $K^b$ were used as negative examples. The entire 310 peptide data base was divided into training and testing sets. In this example, the testing set contained about ⅓ of the total number of peptides. A conjugate gradient procedure (T. Masters, "Practical Neural Network Recipes in C++", Acad. Press Inc. Boston (1993)) was used to determine the ANN weights, whose initial values were uniform pseudo-random numbers with a range of [−0.7, 0.7]. The network performance, defined as the mean square distance between the network output (i.e., predicted binding strength) and experimentally observed value (i.e., the known value of the binding strength), was measured as a function of the number of learning cycles or "epochs". One epoch occurs when the full set of training patterns is presented to the network.

Figure 2:
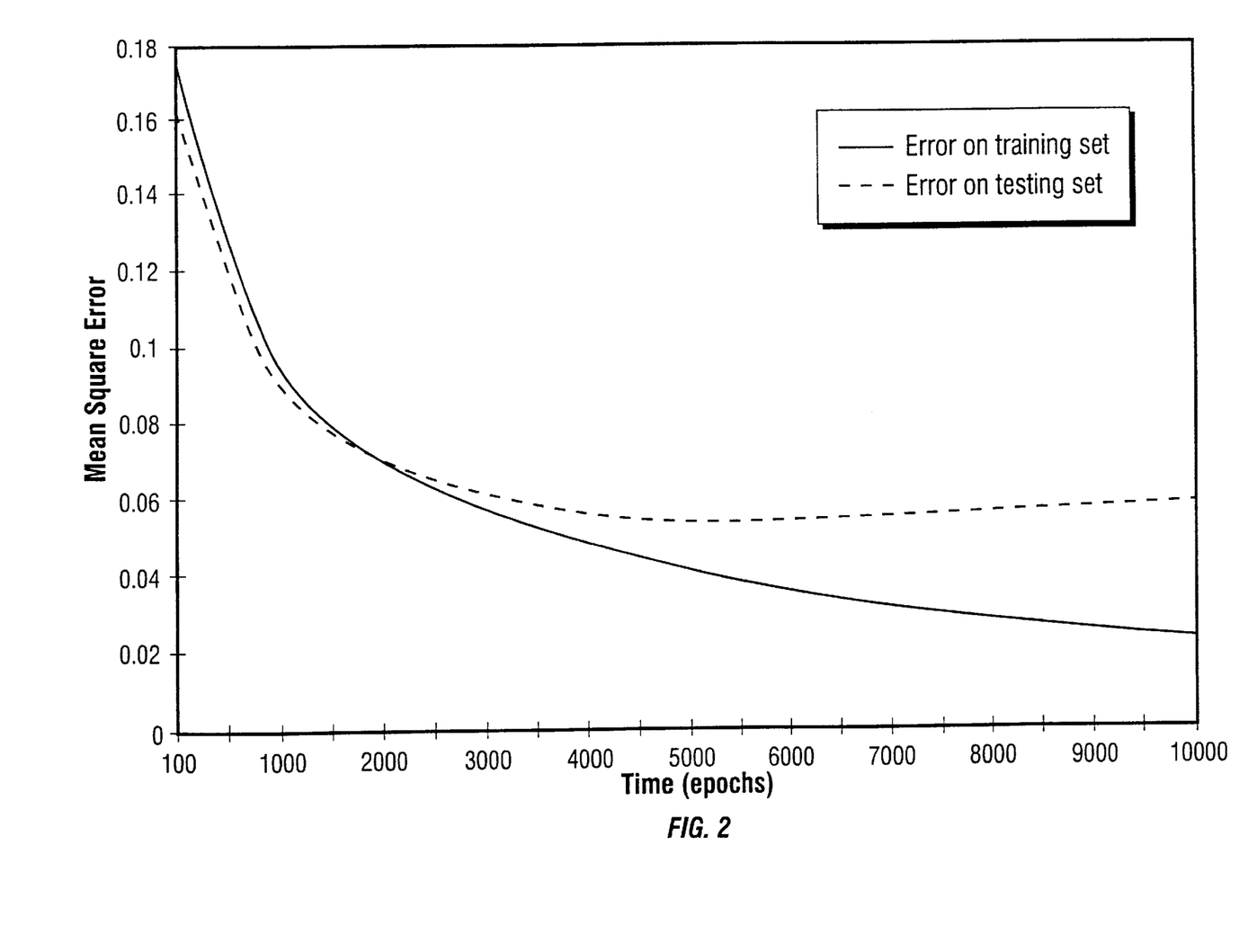
FIG. 2 is a graph showing performance of the ANN on the training and testing sets as a function of training time, measured by the number of times the whole training set was presented to the network (epochs).

FIG. 2 is a graph showing performance of the experimental ANN 1 on the training and testing sets as a function of training time, measured by the number of epochs. As shown in FIG. 2, while the error in the training set decreases monotonically with an increasing number of epochs, the testing set error reaches a minimum and then slowly grows as the ANN memorizes the training set, i.e., as "over fitting" occurs. T. Masters, "Practical Neural Network Recipes in C++", Acad. Press Inc. Boston (1993). Thus, the ANN 1 weights where chosen where the error for the test set was approximately at a minimum. It was empirically determined that 10 hidden units 5 were an optimal number by maximizing the performance on the testing set. Inclusion of an additional hidden layer did not change the performance in this instance.

It is expected that the relationship of the output of the ANN 1 to the experimentally determined binding constant is nonlinear. Experience is required to establish the threshold below which binding would not occur. In the preferred embodiment, the output of the ANN 1 is mapped to such empirical data as three relative classes: strongly binding, weakly binding, and nil binding.

Blind Test of the ANN

The trained ANN 1 was used to predict the binding peptides from the sequence of chicken ovalbumin, a protein containing well characterized $K^b$ epitopes. The 11 strongest, predicted binding peptides are shown in Table 2.

TABLE 2

Comparison of Predicted Binding Peptides with Experiment Results

| Peptide | Amino Acids | ANN | $K_D$ (moles/liter) | FACS Analysis % SIINFEKL |
|---|---|---|---|---|
| 1 | SIINFEKL | 0.46 | 3.0E-9 | 100 |
| 2 | SALAMVYL | 0.44 | 7.1E-9 | 100 |
| 3 | AEERYPIL | 0.36 | 6.7E-5 | 42 |
| 4 | NAIVFKGL | 0.32 | 1.3E-8 | 76 |
| 5 | KVVRFDKL | 0.27 | 2.6E-8 | 94 |
| 6 | RGDKLPGFG | 0.26 | 5.5E-4 | 30 |
| 7 | DVYSFSLA | 0.24 | 7.0E-8 | 65 |

TABLE 2-continued

Comparison of Predicted Binding Peptides with Experiment Results

| Peptide | Amino Acids | ANN | $K_D$ (moles/liter) | FACS Analysis % SIINFEKL |
|---|---|---|---|---|
| 8 | GTMSMLVL | 0.23 | 1.2E-6 | 0 |
| 9 | ASEKMKIL | 0.22 | 5.5E-4 | 4 |
| 10 | DHPFLFCI | 0.20 | 4.7E-5 | 38 |
| 11 | ENIFYCPI | 0.19 | 9.4E-8 | 77 |
| (VSV8) | RGYVYQGL | no data | 4.1E-9 | not applicable |

Following are explanations of each column:

Peptide. Peptides 1–11 are from the ovalbumin sequence listed in order predicted by the ANN 1 to bind $K^b$. VSV8 is the peptide epitope from vesicular stomatitis virus nucleoprotein used as the reporter peptide in competition binding assays (see discussion of FIG. 3 below).

ANN. Relative binding strengths predicted by the ANN 1 defined as the value of the output signal on the second node 7b of the output layer 6. For all sequences presented here, the output value of the first node 7a is 0.7 (the threshold value).

Figure 3:
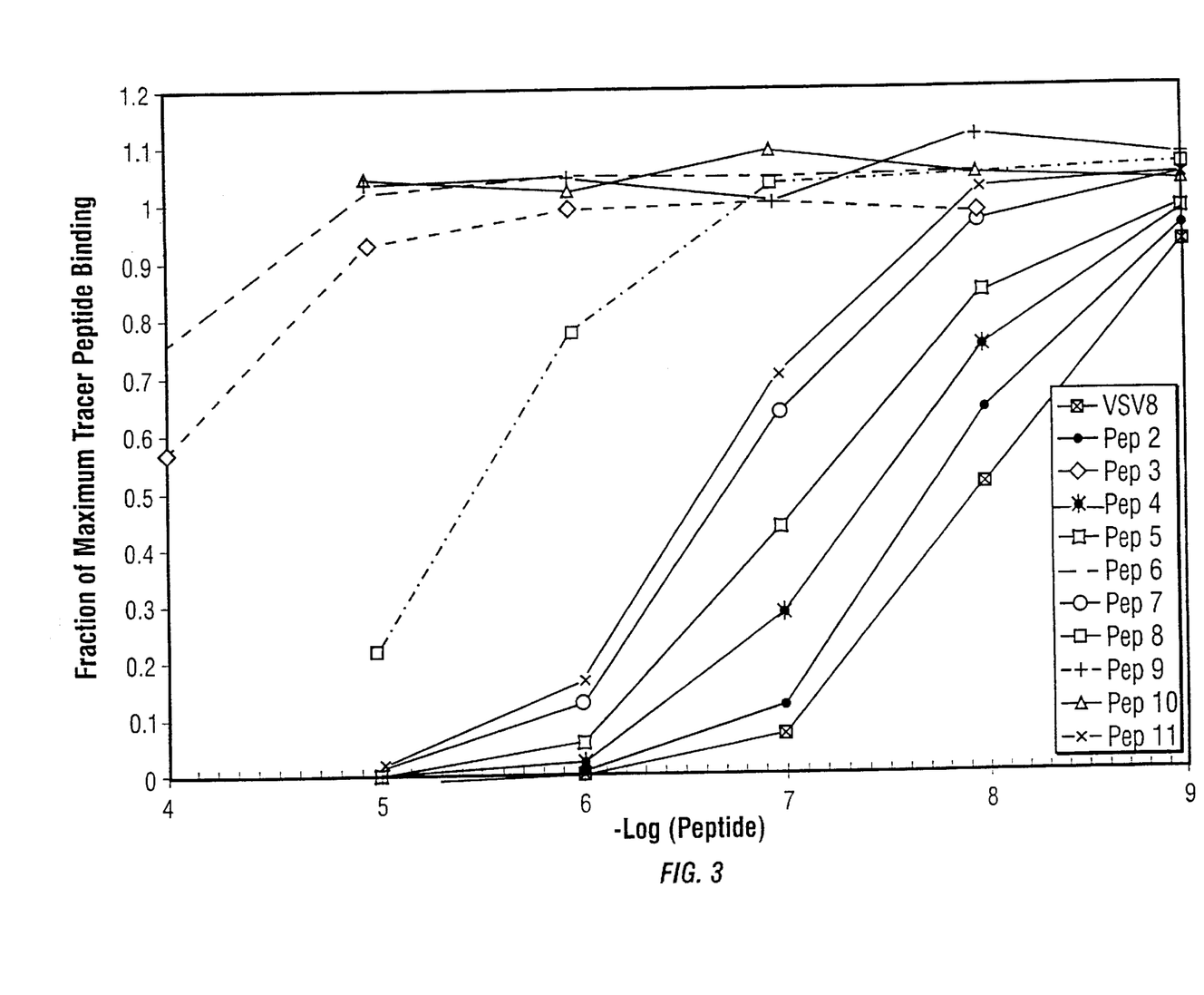
FIG. 3 is a graph showing a competition binding assay.

$K_D$. Dissociation constants of the predicted peptides, in moles/liter. Dissociation curves used to predict the $K_D$ values for peptides 2–11 are shown in FIG. 3. Peptide 1 is the known immunodominant epitope for ovalbumin and has been characterized previously.

FACS Analysis. Values from fluorescence activated cell sorter (FACS) analysis showing the relative amounts of $K^b$ on the surface of $K^b$ transfected drosophila cells following an 18-hour incubation with the indicated peptides. Cells were strained with the anti mouse MHC class 1 antibody Y3 followed by a fluoresceine conjugated second antibody. Median fluorescence values from separate experiments were normalized by subtracting the median fluorescence obtained in the absence of added peptides from each peptide sample and then expressing those values as the percent of the fluorescence obtained with SIINFEKL (which was examined in all experiments).

Validation of ANN Predictions

To experimentally test the predictions, these 11 peptides were synthesized. Experimental binding affinities for $K^b$ were determined by a competition assay previously used to determine the dissociation constants of peptides for mouse class I molecules. M. Matsumura, Y. Saito, M. R. Jackson, E. S. Song and P. A. Peterson, *J. Biol. Chem.* 267(33), 23589 (1992); Y. Saito, P. A. Peterson and M. Matsumura, *J. Biol. Chem.* 268(28), 21309 (1993); R. Miller, *Methods Enzymology,* 92, 589 (1983).

FIG. 2 is a graph showing the competition binding assay for 11 peptides under test. VSV8 (see Table 2) was radio-iodinated (chloramine-T) for use as a tracer peptide. Competitor peptides 2–11 are ANN predicted $K^b$ binding peptides added to 100,000 cpm of the tracer peptide (2.1×10⁻⁴ μM) with concentrations of $K^b$ that, in the absence of competitors, bound about half of the added tracer. The graph shows the concentration dependent inhibition of the tracer peptide binding by the added competitor peptides. The curve labeled VSV8 are the results of a control experiment where the competitor peptide was the same as the tracer. Peptide concentrations are in moles/liter.

Referring again to Table 2, specific peptide epitopes bind to $K^b$ having $K_D$ values below $10^{-7}$ M. Of the first seven peptides predicted to bind the strongest, five bound at biologically significant levels. This translates into a hit rate of slightly better than 70%. For those peptides that bound strongly, their affinities were predicted in the same order as determined experimentally. The other two peptides in this group bound at levels with lesser or equal affinities to the average $K_D$ (40 µM).

In agreement with the experimental analysis, the top two predicted peptides were in fact the strongest binders and included the immunodominant epitope, OVA-8, for $K^b$. This result is significant as there are 20 peptides in the ovalbumin sequence which contain internal anchor residues, and the ANN analysis narrowed this field to one, OVA-8. Moreover, the second best binding peptide contains no anchor amino acids in positions three or five, and thus would not have been predicted using a simple statistical analysis.

Peptide binding was also analyzed by the ability to stabilize cell surface $K^b$ molecules. Empty class I molecules are thermolabile, but they can be stabilized by binding appropriate peptides. Peptides were bound to $K^b$ molecules expressed on the surfaces of $K^b$ transfected Drosophila cells. Their relative binding strengths are indicated by their median fluorescence. As shown in Table 2, at 23° C., the ability of the peptides to stabilize $K^b$ closely mirrored their binding affinities determined by the competition assay.

SUMMARY

A list of 30 binding peptides were predicted along with scores for the predicted relative binding affinities. To evaluate these predictions, the 11 peptides at the top of the list were synthesized and their binding affinities determined experimentally. Our results demonstrate that the ANN 1 can make highly accurate predictions, some of which could not have been predicted manually using extant anchor position based binding rules. Five of the predicted seven best binders bound with good affinity ($K_D<10^{-7}$ nM). Most significantly, the top predicted peptide bound the strongest and is the known immunodominant epitope. Furthermore, despite the fact that the second best predicted peptide lacked internal anchor residues and thus would not have been included in the set of 20 manually predicted sequences, it was shown experimentally to bind with the second strongest affinity. This affinity is greater than four other predicted binding peptides in the top eleven scores, which do contain internal anchor residues.

Two peptides in the top 7 did not bind $K^b$ with significant affinity; the question is why. One possibility is that binding to phage somehow does not accurately simulate peptide binding in all cases. Other possible reasons for these non-binding sequences are that an insufficiently diverse combination of amino acids was present in the positive and negatively selected phage sequences or that the system of encoding amino acids for the ANN did not adequately distinguish the chemical and physical properties of all of the amino acids. These alternatives are presently being analyzed to improve accuracy of the invention. However, the success rate in the top seven predictions shows that the ANN approach works well.

In its present application, the ANN analysis should be able to predict class I binding peptides for an unlimited number of protein antigens. This may further the understanding of the class I molecular structure as it pertains to peptide binding and perhaps further elucidate how these binding interactions pertain to function. More generally, the inventive approach represents but a first application for identifying binding motifs from either peptide or even small molecule (e.g., peptide mimetics) combinatorial libraries. One strength of the invention is that it allows one to generalize and extract the latent information encoded in a random peptide library that has been screened for a particular property or functionality. The results of applying the ANN 1 of the invention may be used to design stronger binding sequences.

Implementation

The ANN 1 of the invention may be implemented in hardware or software, or a combination of both. However, preferably, the invention is implemented in computer programs executing on programmable computers each comprising at least one processor, at least one data storage system (including volatile and non-volatile memory and/or storage elements), at least one input device, and at least one output device. Program code is applied to input data to perform the functions described herein and generate output information. The output information is applied to one or more output devices, in known fashion.

Each program is preferably implemented in a high level procedural or object oriented programming language to communicate with a computer system. However, the programs can be implemented in assembly or machine language, if desired. In any case, the language may be a compiled or interpreted language.

Each such computer program is preferably stored on a storage media or device (e.g., ROM or magnetic diskette) readable by a general or special purpose programmable computer, for configuring and operating the computer when the storage media or device is read by the computer to perform the procedures described herein. The inventive system may also be considered to be implemented as a computer-readable storage medium, configured with a computer program, where the storage medium so configured causes a computer to operate in a specific and predefined manner to perform the functions described herein.

A number of embodiments of the present invention have been described. Nevertheless, it will be understood that various modifications may be made without departing from the spirit and scope of the invention. Accordingly, it is to be understood that the invention is not to be limited by the specific illustrated embodiment, but only by the scope of the appended claims.

What is claimed is:

1. A computer-implemented method for identifying relative binding motifs of peptide-like molecules, comprising the steps of:
   (a) training a computer-implemented artificial neural network (ANN) with input data characterizing a set of training peptide-like molecules, each of known sequence and binding affinity;
   (b) applying to the ANN input data characterizing at least one test peptide-like molecule, each of known sequence but unknown binding affinity;
   (c) analyzing each applied test peptide-like molecule using the ANN to generate a prediction of a relative binding affinity for each test peptide-like molecule, and outputting such prediction.

2. A computer-implemented method for identifying relative peptide binding motifs, comprising the steps of:
   (a) training a computer-implemented artificial neural network (ANN) with input data characterizing a set of training peptides, each of known binding affinity, each peptide comprising a sequence of amino acids, each amino acid being binary coded as having or lacking specific features generally characteristic of amino acids;

(b) applying to the ANN input data characterizing at least one test peptide, each of unknown binding affinity, each peptide comprising a sequence of amino acids, each amino acid being binary coded as having or lacking specific features generally characteristic of amino acids;

(c) analyzing each applied test peptide using the ANN to generate a prediction of a relative binding affinity for each test peptide, and outputting such prediction.

3. The method of claim 2, wherein the set of training peptides include peptides having a binding affinity for major histocompatiblity complex (MHC) class I molecules.

4. The method of claim 3, wherein the peptides included in the set of training peptides have a binding affinity for mouse MHC class I $K^b$.

5. The method of claim 2, wherein the set of test peptides include peptides having a binding affinity for MHC class I molecules.

6. The method of claim 5, wherein the peptides included in the set of test peptides have a binding affinity for mouse MHC class I $K^b$.

7. The method of claims 1 or 2, wherein the ANN comprises a multi-layer perceptron ANN trained by back-propagation of error.

8. A computer-implemented system for identifying relative binding motifs for peptide-like molecules, comprising:

(a) means for training a computer-implemented artificial neural network (ANN) with input data characterizing a set of training peptide-like molecules, each of known sequence and binding affinity;

(b) means for applying to the ANN input data characterizing at least one test peptide-like molecule, each of known sequence but unknown binding affinity;

(c) means for analyzing each applied test peptide-like molecule using the ANN to generate a prediction of a relative binding affinity for each test peptide-like molecule, and output such prediction.

9. A computer-implemented system for identifying relative peptide binding motifs, comprising:

(a) means for training a computer-implemented artificial neural network (ANN) with input data characterizing a set of training peptides, each of known binding affinity, each peptide comprising a sequence of amino acids, each amino acid being binary coded as having or lacking specific features generally characteristic of amino acids;

(b) means for applying to the ANN input data characterizing at least one test peptide, each of unknown binding affinity, each peptide comprising a sequence of amino acids, each amino acid being binary coded as having or lacking specific features generally characteristic of amino acids;

(c) means for analyzing each applied test peptide using the ANN to generate a prediction of a relative binding affinity for each test peptide, and output such prediction.

10. The system of claim 9, wherein the set of training peptides include peptides having a binding affinity for major histocompatiblity complex (MHC) class I molecules.

11. The system of claim 10, wherein the peptides included in the set of training peptides have a binding affinity for mouse MHC class I $K^b$.

12. The system of claim 9, wherein the set of test peptides include peptides having a binding affinity for MHC class I molecules.

13. The system of claim 12, wherein the peptides included in the set of test peptides have a binding affinity for mouse MHC class I $K^b$.

14. The system of claims 8 or 9, wherein the ANN comprises a multi-layer perceptron ANN trained by back-propagation of error.

15. A computer program, residing on a computer-readable medium, for identifying relative binding motifs for peptide-like molecules, comprising instructions for causing a computer to:

(a) train a computer-implemented artificial neural network (ANN) with input data characterizing a set of training peptide-like molecules, each of known sequence and binding affinity;

(b) apply to the ANN input data characterizing at least one test peptide-like molecule, each of known sequence but unknown binding affinity;

(c) analyze each applied test peptide-like molecule using the ANN to generate a prediction of a relative binding affinity for each test peptide-like molecule, and output such prediction.

16. A computer program, residing on a computer-readable medium, for identifying relative peptide binding motifs, comprising instructions for causing a computer to:

(a) train a computer-implemented artificial neural network (ANN) with input data characterizing a set of training peptides, each of known binding affinity, each peptide comprising a sequence of amino acids, each amino acid being binary coded as having or lacking specific features generally characteristic of amino acids;

(b) apply to the ANN input data characterizing at least one test peptide, each of unknown binding affinity, each peptide comprising a sequence of amino acids, each amino acid being binary coded as having or lacking specific features generally characteristic of amino acids;

(c) analyze each applied test peptide using the ANN to generate a prediction of a relative binding affinity for each test peptide, and output such prediction.

17. The computer program of claim 16, wherein the set of training peptides having a binding affinity for major histocompatiblity complex (MHC) class I molecules.

18. The computer program of claim 17, wherein the peptides included in the set of training peptides have a binding affinity for mouse MHC class I $K^b$.

19. The computer program of claim 16, wherein the set of test peptides include peptides having a binding affinity for MHC class I molecules.

20. The computer-program of claim 19, wherein the peptides included in the set of test peptides have a binding affinity for mouse MHC class I $K^b$.

21. The computer program of claims 15 or 17, wherein the ANN comprises a multilayer perceptron ANN trained by back-propagation of error.

* * * * *

REEXAMINATION CERTIFICATE (4489th)

United States Patent
Skolnick et al.

(10) Number: US 5,933,819 C1
(45) Certificate Issued: Nov. 13, 2001

(54) PREDICTION OF RELATIVE BINDING MOTIFS OF BIOLOGICALLY ACTIVE PEPTIDES AND PEPTIDE MIMETICS

(75) Inventors: Jeffrey Skolnick; Mariusz Milik, both of San Diego, CA (US); Andrezej Kolinski, Warsaw (PL)

(73) Assignee: The Scripps Research Institute, La Jolla, CA (US)

Reexamination Request:
No. 90/005,553, Nov. 24, 1999

Reexamination Certificate for:
Patent No.: 5,933,819
Issued: Aug. 3, 1999
Appl. No.: 08/862,192
Filed: May 23, 1997

(51) Int. Cl.[7] .................................................. G06F 15/18
(52) U.S. Cl. ............................................... 706/21; 706/31
(58) Field of Search ........................................ 706/21, 31

(56) References Cited

PUBLICATIONS

Livingstone, C. D. et al., *Computer Applications in the Biosciences*, 9(6): 745–756, 1993.*
Holley et al., *Methods of Enzymology*, 202: 204–224, 1991.*
Taylor et al., *Journal of Theoretical Biology*, 119(1): 205–218, 1986.*
Milik et al., *Nature Biotechnology*, 16: 753—756, Aug. 1998.*
Masters, T., *Practical Neural Network Recipes in C++*, Academic Press Inc., Boston, 1993.*
Tomii, K. et al., *Protein Engineering*, 9 (1): 27–36, 1996.*
Prediction of Binding to MHC Class I Molecules, Adams et al. Journal of Immunological Methods (Apr. 1995) pp. 181–190.*
Predicition of MHC Binding Peptides Using Artificial Neural Networks, Brusic et al. Complex Systems: Mechanism of Adaptation, pp. 253–260. Sep. 1994.*

* cited by examiner

Primary Examiner—Marianne P. Allen (57) ABSTRACT

A general neural network based method and system for identifying peptide binding motifs from limited experimental data. In particular, an artificial neural network (ANN) is trained with peptides with known sequence and function (i.e., binding strength) identified from a phage display library. The ANN is then challenged with unknown peptides, and predicts relative binding motifs. Analysis of the unknown peptides validate the predictive capability of the ANN.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–21 are cancelled.

\* \* \* \* \*